(12) United States Patent
Kobler et al.

(10) Patent No.: US 8,158,186 B2
(45) Date of Patent: Apr. 17, 2012

(54) 2-METHYLTHIOETHYL-SUBSTITUTED HETEROCYCLES AS FEED ADDITIVES

(75) Inventors: Christoph Kobler, Alzenau (DE); Philipp Roth, Hanau (DE); Christoph Weckbecker, Gruendau-Lieblos (DE); Klaus Huthmacher, Gelnhausen (DE)

(73) Assignee: Evonik Degussa GmbH, Essen (DE)

( * ) Notice: Subject to any disclaimer, the term of this patent is extended or adjusted under 35 U.S.C. 154(b) by 551 days.

(21) Appl. No.: 12/339,284

(22) Filed: Dec. 19, 2008

(65) Prior Publication Data

US 2009/0162474 A1    Jun. 25, 2009

Related U.S. Application Data

(60) Provisional application No. 61/074,846, filed on Jun. 23, 2008.

(30) Foreign Application Priority Data

Dec. 21, 2007 (DE) .................. 10 2007 062 199

(51) Int. Cl.
*A23J 1/00* (2006.01)
*C07D 263/04* (2006.01)
*C07D 317/34* (2006.01)

(52) U.S. Cl. ........ 426/656; 548/225; 548/226; 549/229; 549/296

(58) Field of Classification Search .................. 426/656; 548/225; 549/229, 296
See application file for complete search history.

(56) References Cited

FOREIGN PATENT DOCUMENTS

| | | | |
|---|---|---|---|
| DE | 2324591 | * | 12/1974 |
| WO | WO 99/04647 | | 2/1999 |
| WO | WO 00/28835 | | 5/2000 |
| WO | WO 01/56980 A1 | | 8/2001 |
| WO | WO 01/58864 A1 | | 8/2001 |
| WO | WO 2004/008874 A1 | | 1/2004 |

OTHER PUBLICATIONS

Hidetoshi Tokuyama, et al., "Reduction of Ethanethiol Esters to Aldehydes", Practical Synthetic Procedures, Bd. 8, XP002517494, 2002, pp. 1121-1123.
Steven C. Loerch, et al., "Rumen Protected Amino Acids in Ruminant Nutrition", Absorption and Utilization of Amino Acids, vol. III, 1989, pp. 187-200.
B. Graulet, et al., "The Isopropyl ester of Methionine Hydroxy-Analogue is Absorbed Through the Rumen Wall in the Cow", Journal of Animal and Feed Sciences, 13, Suppl. 1, 2004, 269-272.

* cited by examiner

*Primary Examiner* — Andrew D Kosar
*Assistant Examiner* — Karen Cheng
(74) *Attorney, Agent, or Firm* — Oblon, Spivak, McClelland, Maier & Neustadt, L.L.P.

(57) ABSTRACT

A chemical compound of the general formula I or II is useful as feed additive:

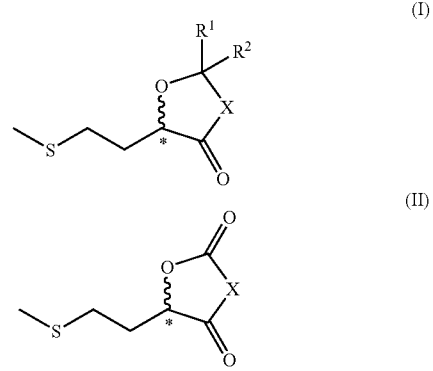

wherein X=O or NR, and R=H, $C_1$-$C_6$-alkyl (optionally branched), $C_3$-$C_6$-cycloalkyl, aryl, or aralkyl, and wherein $R^1$, $R^2$, are identical or different and in each case H, $C_1$-$C_6$-alkyl (optionally branched), $C_3$-$C_6$-cycloalkyl, allyl, aryl, or aralkyl; or $R^1$ and $R^2$ together are an $C_2$- to $C_6$-alkylene group (optionally $C_1$-$C_6$-alkyl substituted).

36 Claims, No Drawings

2-METHYLTHIOETHYL-SUBSTITUTED HETEROCYCLES AS FEED ADDITIVES

BACKGROUND OF THE INVENTION

1. Field of the Invention

The present invention relates to novel 2-methylthioethyl-substituted heterocycles, their derivatives, method of production and use as feed additive.

2. Description of the Related Art

Essential amino acids such as methionine, lysine or threonine are, as feed additives, very important components of animal nutrition. Their supplementation makes possible, firstly, more rapid growth of the animals, but secondly also more efficient feed utilization. This is a great economic advantage. The markets for feed additives are of great industrial and economic importance. In addition, they are strong growth markets due, not least, to the increasing importance of countries such as, for example, China and India.

WO 2004008874 discloses, inter alia, that methionine (2-amino-4-methylthiobutyric acid) is the first limiting amino acid for many animal species. For instance, in dairy cattle, for example, efficient milk production with respect to the amount and quality is greatly dependent on a sufficient feed of methionine. The methionine requirement of high-performance dairy cattle cannot be covered in this case by the microbial protein formed in the rumen or by protein from the feed which is not broken down in the rumen (Graulet et al., *J. Animal and Feed Sciences* (2004), 269). It is therefore advantageous to supplement methionine to the feed in order to increase the economic efficiency of milk production and quality of the milk.

In the case of monogastric animals such as, for example, poultry and pigs, D,L-methionine and the Methionine Hydroxy Analog (MHA) having the chemical name D,L-2-hydroxy-4-methylthiobutyric acid (HMB), are conventionally used as feed additives. The available amount of L-methionine is thereby increased in the organism which is then available to the animal for growth.

In contrast thereto, supplementation of the feed with methionine is not effective in ruminants, since the majority is broken down by microbes in the rumen of ruminants. Owing to this breakdown, therefore, only a fraction of the supplied methionine passes into the small intestine of the animal, where generally the methionine is absorbed into the blood.

WO 99/04647 describes the use of MHA for ruminants. Therein it is asserted that MHA is only partly broken down in the rumen and therefore at least 20-40% of the supplemented MHA, after absorption in the small intestine, can pass into the metabolism. In numerous other publications, in contrast, the mode of action of MHA in ruminants is discussed differently. Thus, for example, WO 200028835 describes that MHA can only successfully pass through the rumen and finally arrive in the small intestine for absorption when MHA is administered in very large amounts of 60-120 g/day/animal. However, this is no longer economically efficient.

In order that methionine products such as D,L-methionine or rac-MHA are available to ruminants with high efficiency, a form protected from rumen breakdown must be used. The challenge in this case is to find a suitable methionine product which gives the methionine a rumen stability which is as high as possible and nevertheless ensures high and efficient absorption of the methionine in the intestine. In this case there are a plurality of possibilities of giving the D,L-methionine or rac-MHA these properties:

a) Physical Protection:

By applying a suitable protective layer or distributing the methionine in a protective matrix, a high rumen stability can be achieved. As a result the methionine can pass through the rumen virtually without loss. In the further course, the protective layer is then opened or removed, for example, in the abomasum by acid hydrolysis and the released methionine can then be absorbed by the animal in the small intestine. The protective layer or matrix can consist of a combination of a plurality of substances such as, for example, lipids, inorganic materials and carbohydrates. For example, the following product forms are commercially available:

i) Met-Plus™ from Nisso America, is a lipid-protected methionine having a D,L-methionine content of 65%. The protective matrix consists of the calcium salts of long-chain fatty acids such as, for example, lauric acid. Butylated hydroxytoluene acts as preservative.

ii) Mepron® M85 from Degussa AG is a carbohydrate-protected methionine which has a core of D,L-methionine, starch and stearic acid. Ethylcellulose is used as protective layer. The product has a content of 85% D,L-methionine.

iii) Smartamine™ M from Adisseo is a polymer-protected methionine. The pellets, in addition to stearic acid, contain at least 70% D,L-methionine. The protective layer contains vinylpyridine-styrene copolymer.

Although physical protection prevents the microbial breakdown of methionine in the rumen and as a result the supply and utilization of methionine can be increased in the animal, there are some serious disadvantages.

The production or coating of methionine is usually a technically complicated and complex process and is therefore expensive. In addition, the surface coating of the finished pellets can easily be damaged by mechanical stress and abrasion during feed administration, which can lead to reduction or complete loss of the protection. Therefore, it is also not possible to process the protected methionine pellets into a larger mixed-feed pellet and repellet them, since as a result, again the protective layer would break up by the mechanical stress. This greatly restricts the use of such products, since the mixed feed pelletting is a widespread method of feed processing.

b) Chemical Protection:

Increased rumen stability of methionine can, in addition to the purely physical possible methods of protection, also be achieved by modifying the chemical structure, for example by esterifying the carboxylic acid group. Currently, the following products are commercially available or are described in the literature:

i) Methionine esters such as, for example, D,L-tert-butyl-methionine: The esters were tested and demonstrated only moderate rumen stability (Loerch and Oke; "Rumen Protected Amino Acids in Ruminant Nutrition" in "Absorption and Utilization of Amino Acids" Vol. 3, 1989, 187-200, CRC Press Boca Raton, Fla.). For D,L-tert-butylmethionine, in contrast, in WO 0028835, a biological value of 80% was published.

ii) Metasmart™ from Adisseo is the racemic isopropyl ester of MHA (HMBi). This compound is also marketed under the trademark "Sequent" by the American company Novus. WO 00/28835 published a biological value of at least 50% for HMBi in ruminants. In this case, especially, the surprisingly rapid absorption of the hydrophobic HMBis through the rumen wall plays a decisive role. The ester can then be hydrolyzed to MHA in the blood and, after oxidation and subsequent transamination, converted to L-methionine.

Patent EP 1358805 published a comparable biological value for HMBi. In these studies, HMBi was applied to a porous carrier. In a further publication, the European Commission reported that again approximately 50% HMBi is absorbed through the rumen wall (European Commission: Report of the Scientific Committee on Animal Nutrition on the Use of HMBi; 25 Apr. 2003). Graulet et al. published in 2004 in the Journal of Animal and Feed Science (269), the fact that via the lipophilic properties of the isopropyl group of HMBi, better diffusion through the rumen wall is made possible.

For the production of HMBi, two different processes have been published. For instance, HMBi, on the one hand, can be synthesized directly in one stage from the corresponding cyanohydrine (WO 00-59877). The esterification to give the isopropyl ester proceeds in this case in situ, without MHA having to be isolated in advance. Another process, in contrast, esterifies pure MHA with isopropanol (WO 01-58864 and WO 01-56980). In both cases, for the synthesis, Prussic acid is used which is expensive and, in addition, involves a great hazard potential.

The aquafarming sector (Food and Agriculture Organization of the United Nation (FAO) Fisheries Department "State of World Aquaculture 2006", 2006, Rome. International Food Policy Research Institute (IFPRI) "Fish 2020: Supply and Demand in Changing Markets", 2003, Washington, D.C.) has also recently acquired importance. The culture of edible saltwater and freshwater animals, in particular fish and crustacea, likewise requires particular product forms for supply with methionine.

The supply of fish and crustacea which are held commercially in aquacultures, requires a correspondingly protected product form, firstly in order that the product during feed administration remains sufficiently stable in the aqueous environment and secondly in order that the methionine product finally taken up by the animal can be optimally utilized in the animal organism.

BRIEF DESCRIPTION OF THE PREFERRED EMBODIMENTS

It was an object of the present invention to provide a feed and a feed additive in animal nutrition based on novel methionine substitutes.

Against the background of the disadvantages of the background art, it was especially the object to provide a chemically protected methionine product for farm animals. In particular, this product should be rumen-stable for use for ruminants, especially for dairy cattle. The product should also be as suitable as possible for use in the nutrition of fish and crustacea in aquacultures. In this manner, in addition to D,L-methionine and MHA, a further efficient methionine source should be made available to the animals, which as far as possible does not have the disadvantages of the known products, or has them only to a slight extent.

A further object was to find a feed and a feed additive having very high biological value and which should have good handleability and storability and also stability under the conventional conditions of mixed-feed processing, in particular pelletting. In the case of ruminants, such a product would have the advantage of a significantly simpler and standardized mixed-feed processing/provision, so that the economic efficiency and also the quality, of milk production would thereby be increased.

These objects and also further objects which are not mentioned explicitly, but which can readily be derived or concluded from the context discussed herein are achieved by the heterocyclic compounds according to the invention and derivatives thereof according to formula I and formula II, in particular use thereof as feed, preferably for hens, pigs, ruminants, fish and crustacea.

The present invention therefore relates to a chemical compound of the general formula (I) or (II),

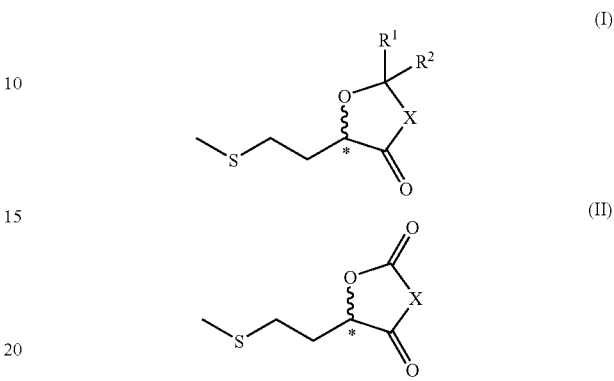

wherein X=O or NR, and R=H, an optionally branched $C_1$-$C_6$-alkyl, $C_3$-$C_6$-cycloalkyl, aryl, in particular phenyl, or aralkyl, in particular benzyl, and wherein $R^1$, $R^2$, are identical or different and in each case H, an optionally branched $C_1$-$C_6$-alkyl, $C_3$-$C_6$-cycloalkyl, allyl, aryl, in particular phenyl, or aralkyl, in particular benzyl, or $R^1$ and $R^2$ together are an optionally $C_1$-$C_6$-alkyl substituted $C_2$- to $C_6$-alkylene group.

The advantages of the compound I, are that, e.g., for $R^1$, $R^2$=H or =low-alkyl residues such as methyl, ethyl, n-propyl, they are liquid, water-clear colorless components. Secondly, the components of the formula I are free from dimeric and oligomeric byproducts, quite in contrast to the commercially available 2-hydroxy-4-methylthioethylbutyric acid (MHA monomer). This is in equilibrium with its dimeric and higher oligomeric esters (condensation products) which have a significantly lower bioavailability than MHA monomer or D,L-methionine itself. MHA is therefore, similarly to the analogous lactic acid, marketed as an 88 percent strength aqueous solution in order to influence the equilibrium in the direction of the desired monomer.

The components according to the invention, in contrast, do not need to be diluted with water, so that the pure active compound is available. Furthermore, they can readily be distilled, particularly in the case of $R^1$, $R^2$=H, methyl, ethyl, n-propyl, so that a virtually 100% purity of these novel substances can be achieved in a manner which is technically simple to carry out, which is an extraordinary processing advantage, and therefore also economic advantage.

The liquid compounds I and II, in each case where X=O, can be used directly as liquid feed additive, which offers advantages for certain applications, in particular when in mixed feed operations, liquid metering systems for what are termed microcomponents are already available. Optionally, these components, however, can also be applied to solid carriers which can be inorganic or organic in nature and should be suitable for feeds and thus a solid feed additive can be generated in a simple manner which can be handled as easily as, for example, D,L-methionine, as a classic solid feed additive, where only solid metering systems are available.

Such inorganic carriers can be silicas, such as, for example, Sipemat from Evonik-Degussa, or silicates, and also aluminas or zeolites, e.g. calcium, sodium, or sodium aluminum silicate, or metal carbonates such as magnesium, calcium or sodium carbonate, individually or in a mixture of two or more such carriers.

Such organic carriers can be, for example, alginates, stearates, starches and gums. Preference is given to calcium, sodium or aluminum alginate, calcium or sodium stearate, corn starch or gum Arabic, individually or in a mixture of two or more such carriers.

In this manner, a concentration lower than 100% of the component according to the invention can also be set in a targeted manner, if this is wanted.

Preference is given to compounds of the formula I where X=O, since these are both acetals and esters and here in the hydrolysis in the organism, monomeric MHA is formed directly, which can subsequently be metabolized. In this case the corresponding carbonyl compound $R^1R^2C=O$ is released simultaneously.

Preference is given here to compounds of the formula I, where $R^1$ and $R^2$ are each an optionally branched $C_1$-$C_6$-alkyl. For physiological reasons, the compound 4 having $R^1=R^2=CH_3$ is particularly preferred here, since in the MHA release, only acetone is formed, which is physiologically harmless. Owing to the low concentration of typically 0.1 to 0.5% by weight methionine equivalent in the mixed feed, however, other radicals $R^1$, $R^2$ and the carbonyl compounds correspondingly released in the hydrolysis to give MHA are also justifiable.

Further preference is therefore given to the compound 2 (cf. examples), where $R^1=R^2=H$ and compound 6 where $R^1=H$ and $R^2=$tert-butyl. Compound I where X=O and $R^1=H$, $R^2=$phenyl is also preferred here, since in its hydrolysis benzaldehyde is formed, which also occurs in plant products such as bitter almonds. In the hydrolysis of 2, as carbonyl compound, formaldehyde is formed which is readily further oxidized to formate, which itself has importance as a feed ingredient.

Likewise further preference is given to a compound 7 of the general formula I in which $R^1$ and $R^2$ together=$(CH_2)_5$, such that on its hydrolysis cyclohexanone is released.

Preferred compounds in the context of the present invention are also compounds of the formula I where X=NH. On its hydrolysis, in addition to the corresponding carbonyl compound $R^1R^2C=O$, ammonia is released at the same time. This ammonia is exactly the molar $NH_3$ equivalent which is used in the organism for metabolizing the compound II according to the invention to give the amino acid methionine.

Preference is given in this case to compound I where X=NH and $R^1=R^2=H$. On their hydrolysis, as carbonyl compound formaldehyde is formed which is readily further oxidized to formate which itself is of importance as a feed ingredient.

Preference is also given to compound 12 where $R^1=H$ and $R^2=$phenyl. On its hydrolysis, as carbonyl compound, benzaldehyde is formed which is a natural component of bitter almonds.

Preference is also given to compounds of the formula I where X=NH, in which $R^1$ and $R^2$ are each an optionally branched $C_1$-$C_6$-alkyl.

In this case very particular preference is given to compound 10 where $R^1=R^2=CH_3$ and on its hydrolysis only $NH_3$ and acetone are released.

However, compound 13 where $R^1=CH_3$ and $R^2=C_2H_5$ and compound 14 where $R^1$ and $R^2$ together=$(CH_2)_5$ are also novel interesting feed ingredients.

In addition, compound 8 was found having the formula II, where X=O. This substance is liquid at room temperature. Hydrolysis leads directly to the monomer MHA and as byproduct gives only $CO_2$, which in any case occurs in the natural metabolism of living creatures and is therefore completely harmless. This is an extraordinary advantage for animal nutrition.

The counterpart thereto which is interesting in the same manner is compound 15 having the formula II and X=NH, which is a colorless solid. Hydrolysis leads likewise directly to the MHA monomer (2-hydroxy-4-methylthioethylbutyric acid) and, in addition to $CO_2$, as a further byproduct also gives $NH_3$, which likewise occurs in natural metabolism of living creatures and again is ready as $NH_3$ equivalent for the amino acid formation from the hydroxy acid MHA monomer and therefore can offer even further advantages.

All compounds of the general formulae I and II according to the invention are suitable in principle for the use for nutrition of farm animals since all contain the parent substance of the methioninehydroxy analog which, on physiological metabolism of the compounds is released as 2-hydroxy-4-methylthiobutyrate and is finally reacted to give methionine. Further advantages of such chemically protected methionine analogs have been described at the outset and hereinbefore. Such chemically protected product forms are, firstly sufficiently stable during feeding and also in the aqueous environment, and secondly utilizable in the animal organism. Depending on animal species and feed matrix and feed conditions, a person skilled in the art will preferably consider one or other component.

Such compounds can be used in particular for the nutrition of poultry, of pigs, of ruminants, but also for nutrition of fish or crustacea. Feed mixtures for nutrition of farm animals containing at least one of the compounds of the general formulae I or II are also subject matter of the present invention, and also the corresponding use of these compounds for producing feed mixtures for the nutrition of farm animals.

A corresponding process for producing the compounds of the general formulae I or II is also subject matter of the present invention.

Such a process proceeds from a compound of the general formula III,

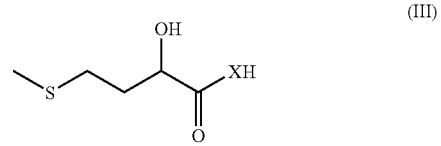

(III)

wherein X, $R^1$ and $R^2$ each have the meaning given above. In the case of X=O, III is 2-hydroxy-4-methylthiobutyric acid (compound 3, MHA monomer) which can also be generated in situ with acid from one of its salts, preferably the calcium salt (compound 1, cf. Example 1). In the case of X=NH, III is 2-hydroxy-4-methylthiobutyramide (compound 9, MHA-amide), which can be obtained from 2-hydroxy-4-methylthiobutyronitrile by known hydrolysis processes, e.g. using 55-70 percent strength sulfuric acid.

The invention therefore relates to a process for producing compounds of the formula I, which comprises reacting a compound of the general formula III with a carbonyl compound $R^1R^2C=O$ in free or acetalated form if appropriate in the presence of a solvent. Suitable solvents in this case are, for example, toluene or chloroform which can act at the same time as entrainers, and also tetrahydrofuran, dioxane, methylene chloride and dimethylformamide. However, it is particularly advantageous to employ the carbonyl compound used simultaneously as solvent, in particular when it is a ketone, such as, for example, in the case of acetone or methyl ethyl ketone. The excess carbonyl compound can readily be recovered in the conventional manner when the reaction is completed and reused directly, if appropriate also after further purification.

Such a process is preferably carried out under acid catalysis. The catalysts used are suitable Lewis acids or Brönstedt acids.

Preferred catalysts are HCl, $H_2SO_4$, p-toluenesulfonic acid, $CF_3SO_3H$ as Brönstedt acids and $ZnCl_2$, $CuSO_4$, $FeCl_3$, $AlCl_3$, $MgCl_2$ and $MgBr_2$ as Lewis acids. The catalysts can be recovered in the conventional manner after completion of the reaction and reused directly, if appropriate after purification.

It is also possible, instead of the carbonyl compound $R^1R^2C=O$, that its dimethylacetal or diethylacetal is used. The resultant methanol or ethanol can be recovered from the reaction mixture, preferably by distillation.

It is also advantageous to remove from the reaction mixture the water which is formed during the condensation reaction on direct use of the carbonyl compound $R^1R^2C=O$.

By removing water or alcohol formed from the reaction mixture, a higher conversion rate and greater selectivity for desired condensation products is achieved. For water/alcohol removal, in addition, also entrainers such as, for example, toluene, can also be used, so that water or alcohols can be removed by distillation in the form of azeotropes.

The invention also relates to a process for producing compounds of the formula II, which comprises reacting a compound of the general formula III

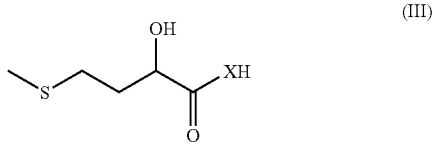

with a carbonic acid derivative $X^1X^2C=O$, wherein $X^1$ and $X^2$ are identical or different and independently of one another can be chlorine or $OCCl_3$, $OCH_3$, $OCH_2CH_3$, or imidazolyl or triazolyl bound via the nitrogen.

In one embodiment, "imidazolyl or triazolyl bound via the nitrogen" refers to different phosgene derivatives for cyclization to form primarily cyclic anhydrides as a product. A very reactive group of phosgene analogs is selected from the group of so-called Staab reagents and are carbonyldiimidazole, preferably of the formula

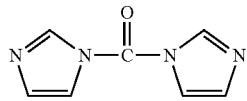

and 4H-1,2,4-triazole of the formula

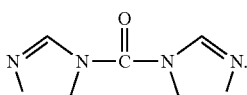

Since phosgene ($X^1$, $X^2$=Cl) is problematic as a reagent, preferably the readily handleable diphosgene ($X^1$=Cl, $X^2$=$OCCl_3$) is used as reactive carbonic acid equivalent. However, dimethyl carbonate or diethyl carbonate and the indicated N-containing carbonic acid equivalents such as, for example, carbonyl diimidazole are also highly suitable and readily handleable.

Such a reaction can advantageously be carried out under not only acid, but also base catalysis. Acid catalysts which can be used are the abovementioned Brönstedt or Lewis acids. Suitable compounds as basic catalysts are, in particular, alkali metal alkoxides of $C_1$-$C_4$-alcohols such as, for example, sodium methoxide or sodium ethoxide or else calcium tert-butylate.

A further suitable process variant for producing compounds of the formula I where X=NH, comprises reacting 2-hydroxy-4-methylthiobutyronitrile of the formula IV

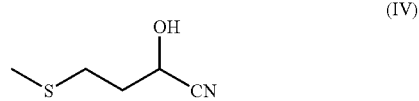

with a carbonyl compound $R^1R^2C=O$ in the presence of acid and a carboxylic anhydride, wherein $R^1$ and $R^2$ have the meaning given above. This has the advantage that the precursor of 2-hydroxy-4-methylthiobutyramide (MHA-amide) is dispensed with.

In such a process variant, the acid used is preferably sulfuric acid and/or acetic acid, and the carboxylic anhydride is preferably acetic anhydride.

All process variants have the advantage that they can be carried out in a simple manner and with in part good to very good yields.

The invention also relates to a method of feeding a farmed animal, comprising feeding the animal with a compound of formula I and/or II. The compounds of formula I and/or II can be administered alone or in combination with other nutrients in the form of a nutritional composition.

Having generally described this invention, a further understanding can be obtained by reference to certain specific examples which are provided herein for purposes of illustration only, and are not intended to be limiting unless otherwise specified.

EXAMPLES

Example 1

Synthesis of 5-(2-(methylthio)ethyl)-1,3-dioxolan-4-one (2) from 2-hydroxy-4-(methylthio)butanoic Acid Calcium Salt (1) and Formalin Solution by Brönstedt Acid Catalysis in a Two-Phase Mixture

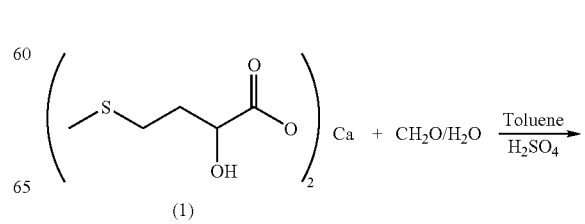

-continued

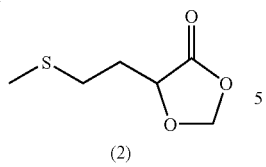

(2)

10.0 g (29.5 mmol) of 2-hydroxy-4-(methylthio)butanoic acid calcium salt (1) were placed in a 500 mL three-neck round bottom flask in 150 mL of water and 150 mL of toluene and admixed with 3.5 g (34.6 mmol) of 97% strength sulfuric acid. After addition of 50 g (0.58 mol, 19.6 eq.) of 37% strength formalin solution, the mixture was heated to boiling temperature and stirred for 16 h at this temperature. After it was cooled, the phases were separated and the aqueous phase was washed twice, each time with 50 mL of toluene. The combined organic phases were washed once with 50 mL of NaCl solution, dried over MgSO$_4$ and concentrated on a rotary evaporator. The resultant crude product was subsequently distilled (boiling point=125° C./1.5 mbar). This produced 7.7 g (47.6 mmol, yield=81%) of 5-(2-(methylthio) ethyl)-1,3-dioxolan-4-one (2) as a colorless liquid.

$^1$H-NMR of 5-(2-(methylthio)ethyl)-1,3-dioxolan-4-one (2) (500 MHz, CDCl$_3$): δ=2.02-2.21 (m, 2H, CH$_2$); 2.12 (s, 3H, SCH$_3$); 2.62-2.72 (m, 2H, SCH$_2$); 4.39-4.41 (m, 1H, CH); 5.44 (s, 1H, CH); 5.55 (s, 1H, CH)

$^{13}$C-NMR of 5-(2-(methylthio)ethyl)-1,3-dioxolan-4-one (2) (125.8 MHz, CDCl$_3$): δ=15.29 (SCH$_3$); 29.38 (SCH$_2$); 29.74 (CH$_2$); 71.49 (CH); 94.26 (OCH$_2$O); 172.80 (C=O)

Elemental analysis for C$_6$H$_{10}$O$_3$S (M=162.21 g/mol): Calculated: C, 44.43; H, 6.21; S, 19.77. Found: C, 44.22; H, 6.36; S 19.69.

Example 2

Synthesis of 5-(2-(methylthio)ethyl)-1,3-dioxolan-4-one (2) from 2-hydroxy-4-(methylthio)butanoic Acid (3) and Trioxane or Paraformaldehyde by Brönstedt Acid Catalysis

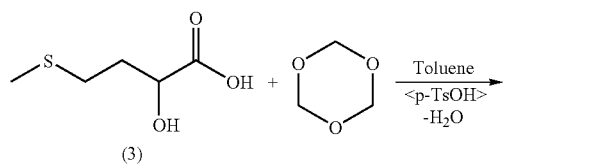

(3)

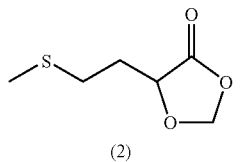

(2)

5.0 g (33.3 mmol) of 2-hydroxy-4-(methylthio)butanoic acid (3) and 5.0 g (55.5 mmol, 1.67 eq.) of 1,3,5-trioxane (alternatively 5.0 g of paraformaldehyde) were placed in a 100 mL three-neck round bottom flask in 50 mL of toluene, admixed with a spatula tip of p-toluenesulfonic acid and heated to boiling. After 12 h, the solvent was distilled off on a rotary evaporator and the resultant crude product was distilled in vacuum. This produced 4.6 g (28.5 mmol, yield=86%) of 5-(2-(methylthio)ethyl)-1,3-dioxolan-4-one (2) as colorless liquid. The NMR data agreed with those from Example 1.

Example 3

Synthesis of 2,2-dimethyl-5-(2-(methylthio)ethyl)-1, 3-dioxolan-4-one (4) from 2-hydroxy-4-(methylthio) butanoic Acid (3) and Acetone by Brönstedt Acid Catalysis

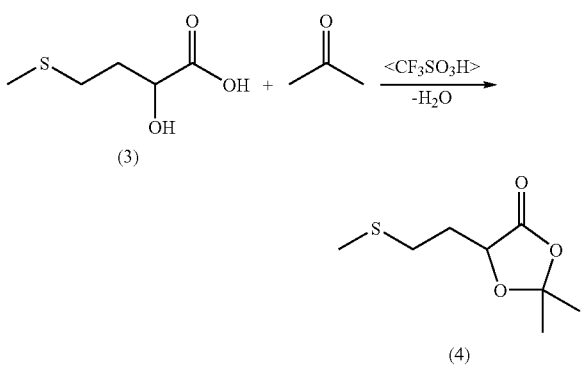

5.0 g (33.3 mmol) of 2-hydroxy-4-(methylthio)butanoic acid (3) were placed in a 250 mL three-neck round bottom flask in 100 mL of acetone, admixed with a few drops of trifluoromethanesulfonic acid or sulfuric acid and stirred at RT for 16 h. Subsequently the reaction mixture was concentrated on a rotary evaporator, taken up into 100 mL of diethyl ether and extracted twice, each time with 25 mL of saturated NaCl solution. The ether phase was dried over MgSO$_4$, concentrated on a rotary evaporator and the resultant crude product subsequently distilled in vacuum via a Vigreux column (boiling point=122° C./1 mbar). This produced 5.2 g (27.4 mmol, yield=82%) of 2,2-dimethyl-5-(2-(methylthio)ethyl)-1,3-dioxolan-4-one (4) as colorless oil.

$^1$H-NMR of 2,2-dimethyl-5-(2-(methylthio)ethyl)-1,3-dioxolan-4-one (4) (500 MHz, CDCl$_3$): δ=1.55 (s, 3H, CH$_3$); 1.61 (s, 3H, CH$_3$); 1.95-2.20 (m, 2H, CH$_2$); 2.11 (s, 3H, SCH$_3$); 2.62-2.66 (m, 2H, SCH$_2$); 4.55 (dd, $^3$J=7.5 Hz, $^2$J=4.4 Hz, 1H, CH)

$^{13}$C-NMR of 2,2-dimethyl-5-(2-(methylthio)ethyl)-1,3-dioxolan-4-one (4) (125.8 MHz, CDCl$_3$): δ=14.96 (SCH$_3$); 25.46 (CH$_3$); 26.92 (CH$_3$); 29.04 (CH$_2$); 30.73 (CH$_2$); 72.18 (CH); 110.37 (C); 172.68 (C=O)

Elemental analysis for C$_8$H$_{14}$O$_3$S (M=190.26 g/mol): Calculated: C, 50.50; H, 7.42; S, 16.85. Found: C, 50.28; H, 7.63; S, 16.88.

Example 4

Synthesis of 2,2-dimethyl-5-(2-(methylthio)ethyl)-1, 3-dioxolan-4-one (4) from 2-hydroxy-4-(methylthio) butanoic Acid (3) and Acetone by Lewis Acid Catalysis

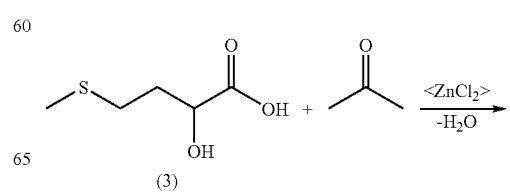

(3)

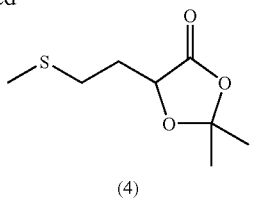

(4)

1.0 g (6.7 mmol) of 2-hydroxy-4-(methylthio)butanoic acid (3) were placed in a 100 mL three-neck round bottom flask in 20 mL of acetone, admixed with 1.0 eq. of Lewis acid (893 mg of $ZnCl_2$, alternatively 1.69 g of $MgBr_2.2Et_2O$ or 1.38 g of $BF_3.2H_2O$) and stirred at RT for 16 h. Subsequently the reaction mixture was concentrated on a rotary evaporator, taken up into 100 mL of diethyl ether, washed with 50 mL of water and twice with 25 mL each time of saturated NaCl solution. The ether phase was then dried over $MgSO_4$, concentrated on a rotary evaporator and the resultant crude product subsequently distilled in vacuum on a Kugelrohr ball-tube apparatus. This produced 1.1 g (5.8 mmol, yield=87%) of 2,2-dimethyl-5-(2-(methylthio)ethyl)-1,3-dioxolan-4-one (4) as colorless oil. The NMR data agreed with those from Example 3.

Example 5

Synthesis of 2,2-dimethyl-5-(2-(methylthio)ethyl)-1,3-dioxolan-4-one (4) from 2-hydroxy-4-(methylthio)butanoic Acid (3) and Acetone by Trans-Ketalization

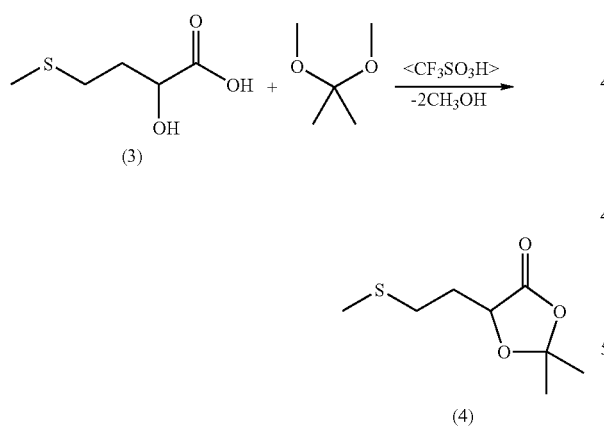

5.0 g (33.3 mmol) of 2-hydroxy-4-(methylthio)butanoic acid (3) and 5.0 g (48.0 mmol, 1.44 eq.) of 2,2-dimethoxypropane were placed in a 100 mL three-neck round bottom flask in 50 mL of tetrahydrofuran and heated to boiling. After 3 h, the solvent was distilled off on a rotary evaporator and the resultant crude product was subsequently distilled in vacuum. This produced 5.6 g (29.7 mmol, yield=89%) of 2,2-dimethyl-5-(2-(methylthio)ethyl)-1,3-dioxolan-4-one (4) as colorless oil. The NMR data agreed with those from Example 3.

Example 6

Synthesis of 2-ethyl-2-methyl-5-(2-(methylthio)ethyl)-1,3-dioxolan-4-one (5) from 2-hydroxy-4-(methylthio)butanoic Acid (3) and Ethyl Methyl Ketone

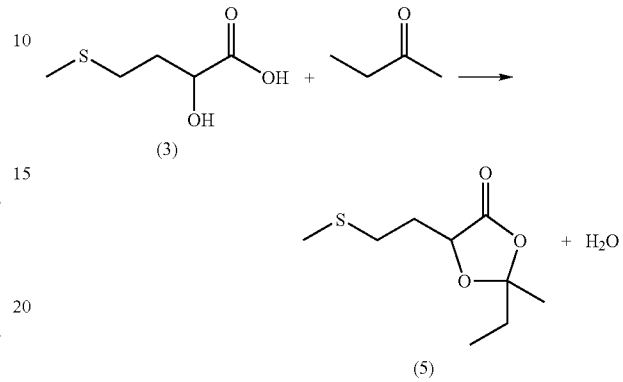

35.0 g (205 mmol) of 88% strength 2-hydroxy-4-(methylthio)butanoic acid (3) were added to 350 mL of ethyl methyl ketone and held under reflux for 5 h. After the mixture was cooled the solvent was taken off together with the resultant water on a rotary evaporator and the residue was distilled in vacuum (boiling point=103° C., 0.4 mbar). This produced 23.5 g (115 mmol, yield=56%) of 2-ethyl-2-methyl-5-(2-(methylthio)ethyl)-1,3-dioxolan-4-one (5) as colorless liquid. The ethyl methyl ketone taken off was dried over $MgSO_4$ and could subsequently be used again for the next reaction.

$^1$H-NMR of 2-ethyl-2-methyl-5-(2-(methylthio)ethyl)-1,3-dioxolan-4-one (5) (diastereomer mixture, ratio 63:37) (500 MHz, $CDCl_3$): δ=0.96-1.00 (m, 3H, $CH_3$); 1.52, 1.56 (s, 3H, $CH_3$); 1.80-1.88 (m, 2H, $CH_2$); 1.97-2.18 (m, 2H, $CH_2$); 2.11 (s, 3H, $SCH_3$); 2.63-2.67 (m, 2H, $CH_2$); 4.54-4.58 (m, 1H, CH)

$^{13}$C-NMR of 2-ethyl-2-methyl-5-(2-(methylthio)ethyl)-1,3-dioxolan-4-one (5) (diastereomer mixture, ratio 63:37) (125.8 MHz, $CDCl_3$): δ=7.23, 7.87 ($CH_3$); 15.24 ($SCH_3$); 23.86, 25.09 ($CH_2$); 29.34, 29.51, 30.97, 31.54, 32.42, 32.60 ($CH_3$, 2×$CH_2$); 72.25, 73.00 (CH); 112.29, 112.83 (C); 173.04, 173.09 (C=O)

Elemental analysis for $C_9H_{16}O_3S$ (M=204.29 g/mol): Calculated: C, 52.91; H, 7.89; S, 15.70. Found: C, 53.04; H, 8.02; S, 15.46.

Example 7

Synthesis of 2-tert-butyl-5-(2-(methylthio)ethyl)-1,3-dioxolan-4-one (6) 2-hydroxy-4-(methylthio)butanoic Acid Calcium Salt (1) and Pivalaldehyde Under Brönstedt Acid Catalysis

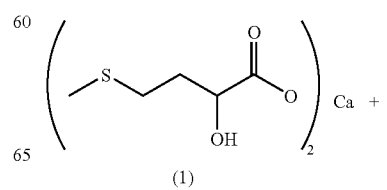

(1)

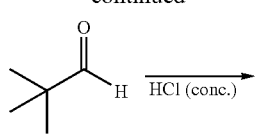 

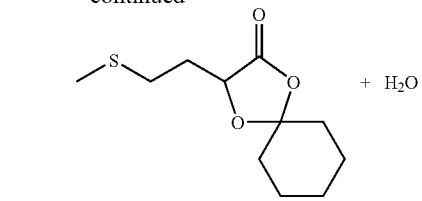

(6)

(7)

6.77 g (20 mmol) of 2-hydroxy-4-(methylthio)butanoic acid calcium salt (1) were slowly admixed with 13.8 g of conc. hydrochloric acid under stirring and ice cooling. A clear solution formed. Subsequently, under a protective gas atmosphere, 15 mL of toluene and 3.45 g (40 mmol) of freshly distilled pivalaldehyde were added, heated to 75° C., wherein the two-phase mixture became clear. Then, the mixture was stirred at this temperature for 7 h. After it had cooled, two phases formed. The organic toluene phases were separated off and the aqueous phase was washed twice, each time with 10 mL of toluene. The combined organic phases were washed three times, each time with 15 mL of water, dried over $Na_2SO_4$ and, after filtration, concentrated on a rotary evaporator. The resultant crude product was subsequently freed from the last solvent residues in high vacuum. This produced 2.62 g (12.0 mmol, yield=30%) of 2-tert-butyl-5-(2-(methylthio)ethyl)-1,3-dioxolan-4-one (6) as slightly yellowish oil.

$^1$H-NMR of 2-tert-butyl-5-(2-(methylthio)ethyl)-1,3-dioxolan-4-one (6) (diastereomer mixture) (500 MHz, $CDCl_3$): δ=0.96, 0.98 (s, 9H, $CH_3$); 1.99-2.22 (m, 2H, $CH_2$); 2.09 (s, 3H, $SCH_3$); 2.64-2.69 (m, 2H, $CH_2$); 4.43-4.46, 4.51-4.54 (m, 1H, CH); 5.15, 5.28 (s, 1H, CH)

$^{13}$C-NMR of 2-tert-butyl-5-(2-(methylthio)ethyl)-1,3-dioxolan-4-one (6) (diastereomer mixture) (125.8 MHz, $CDCl_3$): δ=15.21, 15.25 ($SCH_3$); 23.24, 23.44 ($CH_3$); 29.37, 29.39, 30.22, 30.33, 34.24, 35.74 (C, 2×$CH_2$); 73.15, 73.42 (CH); 109.43, 110.46 (CH); 173.17, 173.27 (C=O)

Elemental analysis for $C_{10}H_{18}O_3S$ (M=218.31 g/mol): Calculated: C, 55.01; H, 8.33; S, 14.69. Found: C, 55.36; H, 8.52; S, 14.23.

Example 8

Synthesis of 3-(2-(methylthio)ethyl)-1,4-dioxaspiro[4.5]decan-2-one (7) from 2-hydroxy-4-(methylthio) butanoic Acid (3) and Cyclohexanone

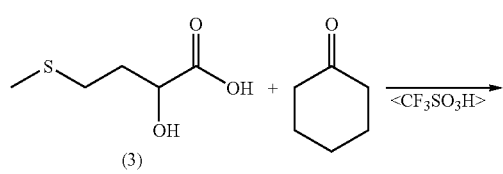

(3)

10.0 g (66.6 mmol) of 2-hydroxy-4-(methylthio)butanoic acid (3) and 13.1 g (133.2 mmol, 2.0 eq.) of cyclohexanone were placed in a 250 mL three-neck round bottom flask in 100 mL of THF, admixed with a few drops of trifluoromethanesulfonic acid and stirred at RT for 16 h. Subsequently the reaction mixture was concentrated on a rotary evaporator. The resultant residue was dissolved with 100 mL of a mixture of 10 mL of dichloromethane and 90 mL of n-hexane and washed twice with 50 mL each time of water and once with 50 mL of saturated NaCl solution. The organic phase was subsequently dried over $MgSO_4$ and concentrated on a rotary evaporator. The resultant crude product was then chromatographed through a silica gel column using n-hexane/ethyl acetate=15:1. After concentration on a rotary evaporator, the last solvent residues were removed in high vacuum. This produced 11.2 g (48.6 mmol, yield=73%) of 3-(2-(methylthio)ethyl)-1,4-dioxaspiro[4.5]decan-2-one (7) as colorless liquid.

$^1$H-NMR of 3-(2-(methylthio)ethyl)-1,4-dioxaspiro[4.5]decan-2-one (7) (500 MHz, $CDCl_3$): δ=1.38-1.88 (m, 10H, 5×$CH_2$); 1.96-2.20 (m, 2H, $CH_2$); 2.11 (s, 3H, $SCH_3$); 2.65 (t, $^3$J=7.4 Hz, 2H, $SCH_2$); 4.55 (dd, $^3$J=7.6, $^2$J=4.5 Hz, 1H, CH)

$^{13}$C-NMR of 3-(2-(methylthio)ethyl)-1,4-dioxaspiro[4.5]decan-2-one (7) (125.8 MHz, $CDCl_3$): δ=22.86 ($SCH_3$); 23.00 ($CH_2$); 24.50 ($CH_2$); 29.38 ($SCH_2$); 31.13 ($CH_2$); 35.24 ($CH_2$); 36.77 ($CH_2$); 72.25 (CH); 111.49 (C); 173.07 (C=O)

Example 9

Synthesis of 5-(2-(methylthio)ethyl)-1,3-dioxolan-2,4-dione (8) from 2-hydroxy-4-(methylthio)butanoic Acid (3) and Diphosgene

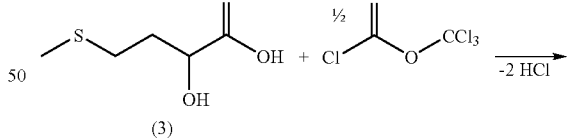

(3)

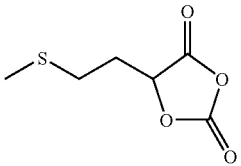

(8)

1.5 g (10.0 mmol) of 2-hydroxy-4-(methylthio)butanoic acid (3) were placed in a 50 mL Schlenk flask in 10 mL of dry THF and under an argon atmosphere, 1.5 mL (12.0 mmol) of diphosgene were added over a period of 15 min. After addition of 30 mg of activated carbon, the reaction mixture was stirred at RT for 12 h. Subsequently the reaction solution was filtered through a Celite bed, concentrated at room temperature on a rotary evaporator and dried for 4 h in high vacuum. This produced 1.1 g (9.7 mmol, yield=97%) of 5-(2-(methylthio)ethyl)-1,3-dioxolan-2,4-dione (8) as yellowish oil.

$^1$H-NMR of 5-(2-(methylthio)ethyl)-1,3-dioxolan-2,4-dione (8) (500 MHz, CDCl$_3$): δ=2.10 (s, 3H, SCH$_3$); 2.20-2.40 (m, 2H, CH$_2$); 2.60-2.80 (m, 2H, SCH$_2$); 5.20-5.30 (m, 1H, CH)

Example 10

Synthesis of 2,2-dimethyl-5-(2-(methylthio)ethyl)oxazolidin-4-one (10) from 2-hydroxy-4-(methylthio)butanamide (9) and Acetone by Brönstedt Acid Catalysis

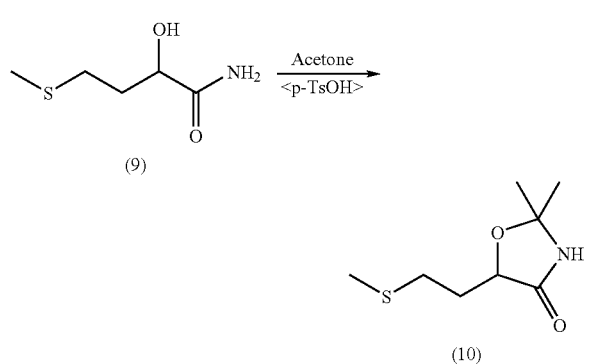

14.9 g (0.1 mol) of 2-hydroxy-4-(methylthio)butanamide (9) in 150 mL of toluene were placed in a 250 mL three-neck flask having a water separator and reflux condenser, admixed with 11.6 g of acetone (0.2 mol) and 0.8 g of p-toluenesulfonic acid and slowly heated to boiling temperature with stirring. The turbid suspension clarified at 90° C. The entire solution was boiled under reflux for 14 h. During this, in total the toluene phase which distilled over was drained off twice and subsequently supplemented twice each time with 11.6 g of acetone. After the mixture had cooled, the turbid reaction solution was filtered and the filtrate was washed once with 100 mL of dilute NaHCO$_3$ solution, twice with 100 mL each time of H$_2$O and subsequently once with 100 mL of saturated sodium chloride solution. Thereafter the toluene phase was dried over Na$_2$SO$_4$. After the filtration the solvent was taken off on a rotary evaporator in vacuum. This produced 13.2 g of an orange-brown oil which slowly crystallized. For recrystallization, 30 mL of n-hexane were added, the mixture was briefly heated to boiling temperature, subsequently cooled to RT, and allowed to stand overnight. On the next day the solid which had crystallized out was filtered off and dried in high vacuum. This produced 11.5 g (0.06 mol, M=189.28 g/mol, yield=60%) of 2,2-dimethyl-5-(2-(methylthio)ethyl)oxazolidin-4-one (8) as a slightly yellowish solid (melting point=84° C.).

$^1$H-NMR of 2,2-dimethyl-5-(2-(methylthio)ethyl)-4-oxazolidinone (10) (500 MHz, DMSO-d6): δ=1.34 (s, 3H, CH$_3$); 1.36 (s, 3H, CH$_3$); 1.73-1.78 (m, 1H, CH); 1.87-1.92 (m, 1H, CH); 2.04 (s, 3H, SCH$_3$); 2.48-2.56 (m, 2H, CH$_2$); 4.23-4.28 (m, 1H, CH); 8.83 (bs, 1H, NH).

$^{13}$C-NMR of 2,2-dimethyl-5-(2-(methylthio)ethyl)-4-oxazolidinone (10) (125.8 MHz, DMSO-d6): δ=14.50 (SCH$_3$); 28.07, 28.70, 29.10, 31.66 (2×CH$_2$, 2×CH$_3$); 74.53 (CH); 89.60 (C); 171.94 (C=O).

Elemental analysis for C$_8$H$_{15}$NO$_2$S (M=189.28 g/mol): Calculated: C, 50.76; H, 7.99; N, 7.40; S, 16.94. Found: C, 50.90; H, 8.11; N, 7.31; S, 16.90.

Example 11

Synthesis of 2,2-dimethyl-5-(2-(methylthio)ethyl)oxazolidin-4-one (10) from 2-hydroxy-4-(methylthio)butanamide (9) by Transketalization

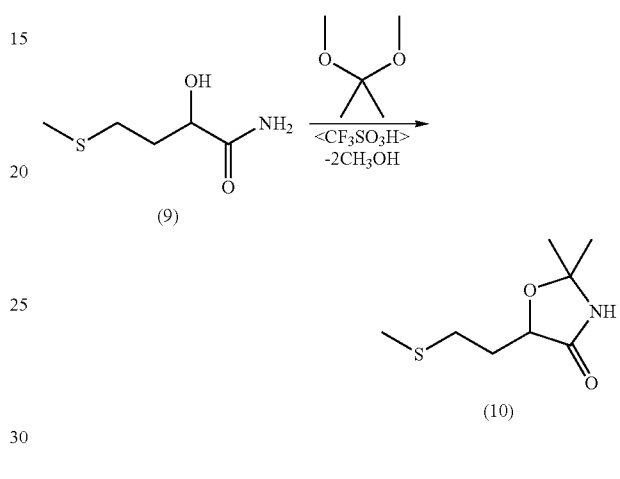

10.0 g (67.0 mmol) of 2-hydroxy-4-(methylthio)butanamide (9) were suspended in 70 mL of dry tetrahydrofuran in a 250 mL three-neck flask and admixed with 13.96 g (134.0 mmol, 2.0 eq.) of dimethoxypropane. After addition of a few drops of trifluoromethanesulfonic acid, the reaction mixture was stirred for 16 h at room temperature. Subsequently the solvent was removed on a rotary evaporator at 100 mbar/30° C. The oily residue was dissolved in 100 mL of diethyl ether and washed twice with 50 mL of water each time. The ether phase was dried over MgSO$_4$ and concentrated on a rotary evaporator. The resultant solid was subsequently recrystallized from 100 mL of n-hexane, filtered off and the last solvent remains were removed in high vacuum. This produced 11.8 g (62 mmol, yield=93%) of 2,2-dimethyl-5-(2-(methylthio)ethyl)oxazolidin-4-one (10) as colorless solid. The NMR data agreed with those of Example 10.

Elemental analysis for C$_8$H$_{15}$NO$_2$S (M=189.28 g/mol): Calculated: C, 50.76; H, 7.99; N, 7.40; S, 16.94. Found: C, 50.96; H, 8.14; N, 7.31; S, 16.88.

Example 12

Synthesis of 2,2-dimethyl-5-(2-(methylthio)ethyl)oxazolidin-4-one (10) from 1-hydroxy-3-(methylthio)propanecarbonitrile (11)

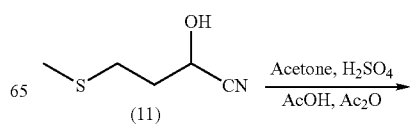

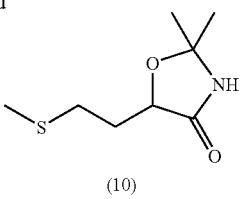

In a 100 mL three-neck flask, 13.1 g of 96% strength 1-hydroxy-3-(methylthio)propanecarbonitrile (11) (0.1 mol) and 7.0 g of acetone (0.12 mol) were dissolved in 30 mL of glacial acetic acid at 10° C. Then, 5 mL of acetic anhydride (0.05 mol) were slowly added dropwise. Subsequently, a mixture of 10 mL of conc. sulfuric acid and 10 mL of glacial acetic acid was added slowly at 0° C. During this it must be ensured that the entire reaction solution does not become warmer than 0° C. This produced a viscous, yellowish, scarcely stirrable suspension. After addition was complete, the mixture was stirred for 1 h at 110° C. and subsequently 15 min at RT. The reaction solution was poured onto ice (approximately 150 g) and thereafter extracted three times with 100 mL of diethyl ether each time. The ether phase was washed once with saturated sodium hydrogencarbonate solution and subsequently with saturated sodium chloride solution and dried over sodium sulfate. The Na$_2$SO$_4$ was filtered off and the ether was taken off in vacuum. This produced 4.5 g of an orange-brown oil which was recrystallized from n-hexane. After filtration and removal of final solvent residues in high vacuum, 2.8 g (14.8 mmol, M=189.28 g/mol, yield=15%) of 2,2-dimethyl-5-(2-(methylthio)ethyl)-4-oxazolidinone (10) were isolated as a slightly yellowish solid. The NMR data agreed with those of Example 10.

Example 13

Synthesis of 5-(2-(methylthio)ethyl)-2-phenyloxazolidin-4-one (12) from 2-hydroxy-4-(methylthio)butanamide (9) by Brönstedt Acid Catalysis

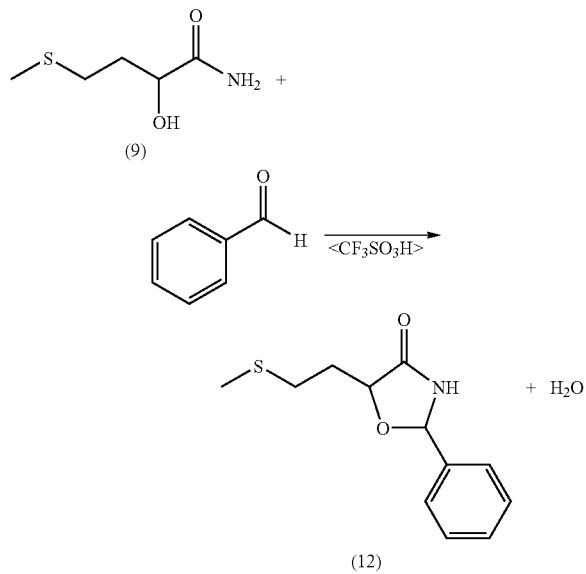

5.0 g (33.5 mmol) of 2-hydroxy-4-(methylthio)butanamide (9) were suspended in 35 mL of dry tetrahydrofuran in a 100 mL three-neck flask and admixed with 7.1 g (67 mmol, 2.0 eq.) of freshly distilled benzaldehyde. After addition of a few drops of trifluoromethanesulfonic acid, the reaction mixture was stirred at room temperature for 16 h. The clear reaction solution was concentrated on a rotary evaporator and the resultant residue taken up in 100 mL of diethyl ether. Subsequently, the mixture was washed thrice each time with 30 mL of water and once with 30 mL of saturated NaCl solution. The ether phase was dried over MgSO$_4$ and concentrated on a rotary evaporator. The resultant product mixture was then separated via fractional crystallization. From 100 mL of dichloromethane/diethyl ether=1:1, in total 2.8 g of a solid was isolated which was subsequently recrystallized from diethyl ether. This produced 2.1 g (8.8 mmol, yield=26%) of 5-(2-(methylthio)ethyl)-2-phenyloxazolidin-4-one (12) as colorless solid (melting point=130° C.).

$^1$H-NMR of 5-(2-(methylthio)ethyl)-2-phenyloxazolidin-4-one (12) (500 MHz, CDCl$_3$): δ=2.00-2.30 (m, 2H, CH$_2$); 2.11 (s, 3H, SCH$_3$); 2.63-2.75 (m, 2H, SCH$_2$); 4.49-4.53 (m, 1H, CH); 6.03-6.05 (m, 1H, CH); 6.24 (bs, 1H, NH); 7.40-7.50 (m, 5H, H$_{Phenyl}$)

$^{13}$C-NMR of 5-(2-(methylthio)ethyl)-2-phenyloxazolidin-4-one (12) (125.8 MHz, CDCl$_3$): δ=19.67 (SCH$_3$); 29.93 (SCH$_2$); 31.74 (CH$_2$); 76.68 (CH); 87.33 (CH); 127.23, 129.28, 130.49, 138.12 (C$_{Phenyl}$); 175.25 (C=O)

Elemental analysis for C$_{12}$H$_{15}$NO$_2$S (M=237.32 g/mol): Calculated: C, 60.73; H, 6.37; N, 5.90; S, 13.51. Found: C, 60.61; H, 6.27; N, 5.66; S, 13.49.

Example 14

Synthesis of 2-ethyl-2-methyl-5-(2-(methylthio)ethyl)oxazolidin-4-one (13) from 2-hydroxy-4-(methylthio)butanamide (9) by Brönstedt Acid Catalysis

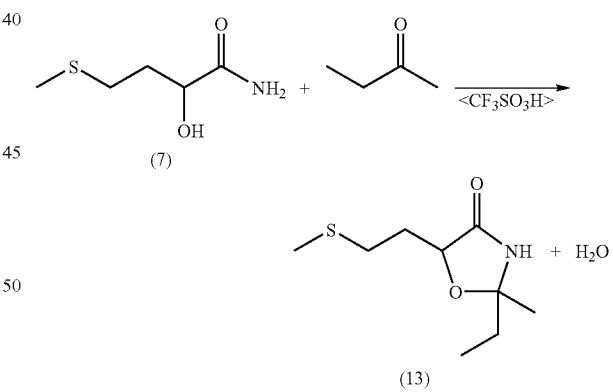

5.0 g (33.5 mmol) of 2-hydroxy-4-(methylthio)butanamide (9) were suspended in 35 mL of dry tetrahydrofuran in a 100 mL three-neck flask and admixed with 4.8 g (67 mmol, 2.0 eq.) of ethyl methyl ketone. After addition of a few drops of trifluoromethanesulfonic acid, the reaction mixture was stirred at room temperature for 5 days. The clear reaction solution was concentrated on a rotary evaporator, the resultant residue taken up in 100 mL of diethyl ether and washed three times with 30 mL of water each time and once with 30 mL of saturated NaCl solution. The combined ether phases were dried over MgSO$_4$, concentrated on a rotary evaporator and the residue was recrystallized twice from a diethyl ether/ n-hexane mixture. This produced 5.1 g (24.9 mmol, yield=74%) of 2-ethyl-2-methyl-5-(2-(methylthio)ethyl)oxazolidin-4-one (13) as a colorless solid (m.p.=62° C.).

$^1$H-NMR of 2-ethyl-2-methyl-5-(2-(methylthio)ethyl)oxazolidin-4-one (13) (diastereomer mixture) (500 MHz, CDCl$_3$): δ=0.95 (t, $^3$J=7.4 Hz, 3H, CH$_3$); 1.44-1.46 (pd, 3H, CH$_3$); 1.62-1.80 (m, 2H, CH$_2$); 1.90-2.16 (m, 2H, CH$_2$); 2.12 (s, 3H, SCH$_3$); 2.60-2.70 (m, 2H, SCH$_2$); 4.42-4.48 (m, 1H, CH); 6.60-6.80 (bd, 1H, NH)

$^{13}$C-NMR of 2-ethyl-2-methyl-5-(2-(methylthio)ethyl)oxazolidin-4-one (13) (diastereomer mixture) (125.8 MHz, CDCl$_3$): δ=7.82, 7.97 (CH$_3$); 15.36, 15.37 (SCH$_3$); 26.55, 27.62, 29.55, 29.78, 31.79, 32.42, 34.09, 34.51 (3×CH$_2$, 1×CH$_3$); 75.18, 76.27 (CH); 92.56, 92.81 (C); 174.13, 174.19 (C=O)

Elemental analysis for C$_9$H$_{17}$NO$_2$S (M=203.30 g/mol): Calculated: C, 53.17; H, 8.43; N, 6.89; S, 15.77. Found: C, 52.46; H, 8.27; N, 6.49; S, 15.71.

Example 15

Synthesis of 2-(2-(methylthio)ethyl)-1-oxa-4-azaspiro[4.5]decan-3-one (14) from 2-hydroxy-4-(methylthio)butanamide (9) by Brönstedt Acid Catalysis

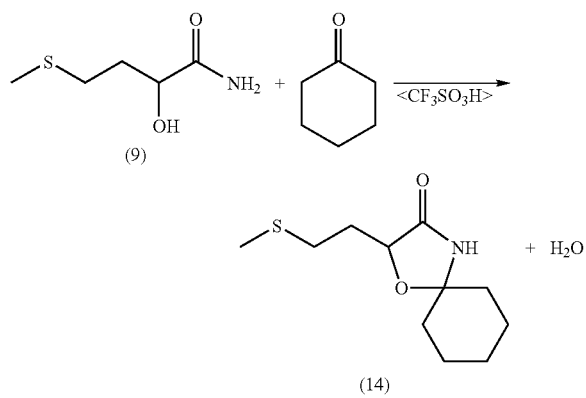

10.0 g (67.0 mmol) of 1-hydroxy-3-(methylmercapto)butanamide (9) were suspended in 150 mL of dry toluene in a 250 mL three-neck flask and admixed with 32.9 g (336 mmol, 5.0 eq.) of cyclohexanone. After addition of a few drops of trifluoromethanesulfonic acid, the reaction mixture was heated to boiling and stirred at this temperature for 1 h. The reaction solution was subsequently cooled and extracted twice, each time with 50 mL of water. The organic phase was dried over MgSO$_4$ and removed on a rotary evaporator at 70 mbar/40° C. The resultant solid was recrystallized from n-hexane/EtOAc, filtered off, dried and the last solvent residues were removed in high vacuum. This produced 12.4 g (54 mmol, yield=80%) of 2-(2-(methylthio)ethyl)-1-oxa-4-azaspiro[4.5]decan-3-one (14) as colorless solid (m.p.=109° C.).

$^1$H-NMR of 2-(2-(methylthio)ethyl)-1-oxa-4-azaspiro[4.5]decan-3-one (14) (500 MHz, CDCl$_3$): δ=1.38-1.80 (m, 10H, 5×CH$_2$); 1.90-2.18 (m, 2H, CH$_2$); 2.12 (s, 3H, SCH$_3$); 2.64 (t, $^3$J=7.6 Hz, 2H, CH$_2$); 4.44 (dd, $^3$J=7.6 Hz, $^2$J=2.1 Hz, 1H, CH); 8.41 (bs, 1H, NH)

$^{13}$C-NMR of 2-(2-(methylthio)ethyl)-1-oxa-4-azaspiro[4.5]decan-3-one (14) (125.8 MHz, CDCl$_3$): δ=15.42 (SCH$_3$); 23.02, 23.12, 24.68 (3×CH$_2$); 29.52 (SCH$_2$); 32.30 (CH$_2$); 37.85, 38.93 (2×CH$_2$); 75.33 (CH); 91.98 (C); 174.54 (C=O)

Elemental analysis for C$_{11}$H$_{19}$NO$_2$S (M=229.34 g/mol): Calculated: C, 57.61; H, 8.35; N, 6.11; S, 13.98. Found: C, 57.72; H, 8.46; N, 5.98; S, 13.99.

Example 16

Synthesis of 5-(2-(methylthio)ethyl)oxazolidin-2,4-dione (15) from 2-hydroxy-4-(methylthio)butanamide (9)

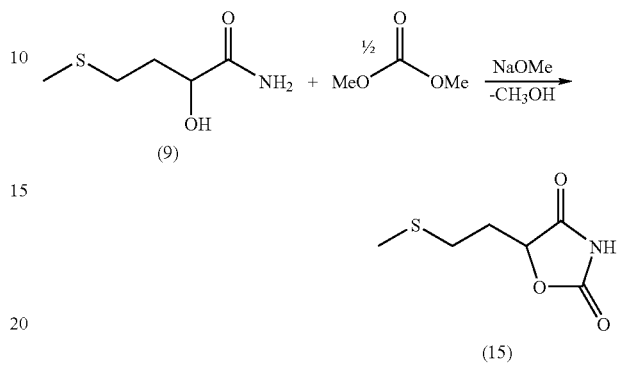

5.0 g (33.5 mmol) of 1-hydroxy-3-(methylmercapto)butanamide (9) were suspended in 50 mL of methanol in a 250 mL three-neck flask, 10 mL of dimethyl carbonate were added and subsequently the mixture was admixed with 9.05 g (168 mmol, 5.0 eq.) of sodium methoxide. The reaction mixture was heated to boiling and stirred at this temperature for 24 h under reflux. The reaction solution was cooled and admixed twice with 100 mL of cold water and extracted three times, each time using 50 mL of tert-butyl methyl ether. The combined organic phase was dried over MgSO$_4$ and concentrated on a rotary evaporator at 15 mbar/40° C. and stored overnight in a refrigerator. The crystallized solid was recrystallized repeatedly from a mixture of n-hexane/EtOAc. After the filtration and drying, the last solvent residues were removed in high vacuum. This produced 2.8 g (12.2 mmol, yield=36.4%) of 5-(2-(methylthio)ethyl)oxazolidin-2,4-dione (15) as colorless solid.

$^1$H-NMR of 5-(2-(methylthio)ethyl)oxazolidin-2,4-dione (15) (500 MHz, CDCl$_3$): δ=2.10 (s, 3H, SCH$_3$); 2.20-2.40 (m, 2H, CH$_2$); 2.60-2.80 (m, 2H, SCH$_2$); 5.0-5.2 (m, 1H, CH); 9.1 (bs, 1H, NH).

German patent application 102007062199.1 filed Dec. 21, 2007 and U.S. provisional patent application 61/074,846, filed Jun. 23, 2008, are incorporated herein by reference.

Numerous modifications and variations on the present invention are possible in light of the above teachings. It is therefore to be understood that within the scope of the appended claims, the invention may be practiced otherwise than as specifically described herein.

The invention claimed is:
1. A compound of the general formula I,

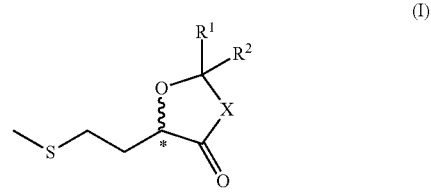

wherein
X=O,
and

R=H, an optionally branched $C_1$-$C_6$-alkyl, $C_3$-$C_6$-cycloalkyl, aryl or aralkyl, and $R^1$, $R^2$, are identical or different and in each case H, $C_1$-$C_6$-alkyl which is optionally branched, $C_3$-$C_6$-cycloalkyl, allyl, aryl, or aralkyl, or $R^1$ and $R^2$ together are $C_2$- to $C_6$-alkylene group which is optionally $C_1$-$C_6$-alkyl substituted.

2. The compound as claimed in claim 1, wherein $R^1=R^2=H$.

3. The compound as claimed in claim 1, wherein $R^1=H$ and $R^2=$tert-butyl.

4. The compound as claimed in claim 1, wherein $R^1=H$ and $R^2=$phenyl.

5. The compound as claimed in claim 1, wherein $R^1$ and $R^2$ are each $C_1$-$C_6$-alkyl which is optionally branched.

6. The compound as claimed in claim 5, wherein $R^1=R^2=CH_3$.

7. The compound as claimed in claim 1, wherein $R^1$ and $R^2$ together=$(CH_2)_5$.

8. A compound of the general formula I,

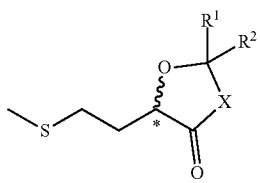

(I)

wherein
X=NR,
R=H, an optionally branched $C_1$-$C_6$-alkyl, $C_3$-$C_6$-cycloalkyl, aryl or aralkyl, and
$R^1$, $R^2$, are identical or different and in each case H, $C_1$-$C_6$-alkyl which is optionally branched, $C_3$-$C_6$-cycloalkyl, allyl, aryl, or aralkyl, or $R^1$ and $R^2$ together are $C_2$- to $C_6$alkylene group which is optionally $C_1$-$C_6$-alkyl substituted.

9. The compound as claimed in claim 8, wherein $R^1=R^2=H$.

10. The compound as claimed in claim 8, wherein $R^1=H$ and $R^2=$phenyl.

11. The compound as claimed in claim 8, wherein $R^1$ and $R^2$ are each $C_1$-$C_6$-alkyl which is optionally branched.

12. The compound as claimed in claim 11, wherein $R^1=R^2=CH_3$.

13. The compound as claimed in claim 11, wherein $R^1=CH_3$ and $R^2=C_2H_5$.

14. The compound as claimed in claim 8, wherein $R^1$ and $R^2$ together=$(CH_2)_5$.

15. A compound of the general formula II

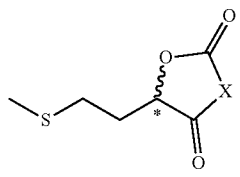

(II)

wherein
X=O,
R=H, an optionally branched $C_1$-$C_6$-alkyl, $C_3$-$C_6$-cycloalkyl, aryl or aralkyl, and $R^1$, $R^2$, are identical or different and in each case H, $C_1$-$C_6$-alkyl which is optionally branched, $C_3$-$C_6$-cycloalkyl, allyl, aryl, or aralkyl, or $R^1$ and $R^2$ together are $C_2$- to $C_6$-alkylene group which is optionally $C_1$-$C_6$-alkyl substituted.

16. A compound of the general formula II

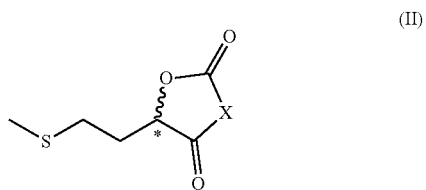

(II)

wherein
X=NH,
R=H, an optionally branched $C_1$-$C_6$-alkyl, $C_3$-$C_6$-cycloalkyl, aryl or aralkyl, and
$R^1$, $R^2$, are identical or different and in each case H, $C_1$-$C_6$-alkyl which is optionally branched, $C_3$-$C_6$-cycloalkyl, allyl, aryl, or aralkyl, or $R^1$ and $R^2$ together are $C_2$- to $C_6$-alkylene group which is optionally $C_1$-$C_6$-alkyl substituted.

17. A feed, comprising:
the compound as claimed in claims 1, 8, 15 or 16;
wherein said feed is suitable for the nutrition of a farmed animals.

18. Feed as claimed in claim 17, wherein said farmed animals are poultry.

19. Feed as claimed in claim 17, wherein said farmed animals are pigs.

20. Feed as claimed in claim 17, wherein said farmed animals are ruminants.

21. Feed as claimed in claim 17, wherein said farmed animals are fish or crustacea.

22. A method of feeding a farm animal, comprising:
feeding a compound as claimed in claims 1, 8, 15 or 16 to said farm animal.

23. A method of producing a feed mixture, comprising:
admixing a compound as claimed in claims 1, 8, 15 or 16 with feed;
said feed mixture being suitable for the nutrition of farm animals.

24. A process for producing a compound of formula I, which comprises:
reacting a compound of the general formula III

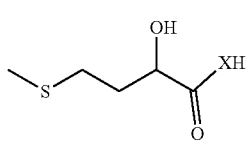

(III)

with a carbonyl compound $R^1R^2C=O$ in free or acetalated form, optionally in the presence of a solvent, to obtain a compound of formula I as claimed in claim 1;
wherein X, $R^1$ and $R^2$ each have the meaning given in claim 1.

25. The process as claimed in claim 24, further comprising adding a Lewis acid or a Brönstedt acid as catalyst.

26. The process as claimed in claim 25, wherein said catalyst is HCl, $H_2SO_4$, p-toluenesulfonic acid, $CF_3SO_3H$, $ZnCl_2$, $CuSO_4$, $FeCl_3$, $AlCl_3$, $MgCl_2$, or $MgBr_2$.

27. The process as claimed in claim 24, wherein the compound $R^1R^2C=O$ is in the form of a dimethylacetal or diethylacetal.

28. The process as claimed in claim 24, further comprising:
removing water or alcohol which is formed during the reacting.

29. A process for producing a compound of formula II, which comprises:
reacting a compound of the general formula III

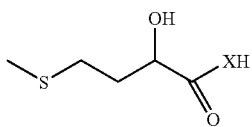

(III)

with a carbonic acid derivative $X^1X^2C=O$, to obtain a compound of formula II as claimed in claim 15;
wherein $X^1$ and $X^2$ are identical or different and independently of one another can be chlorine or $OCCl_3$, $OCH_3$, $OCH_2CH_3$, or imidazolyl or triazolyl bound via a nitrogen in the molecule.

30. The process as claimed in claim 29, wherein $X^1=Cl$ and $X^2=OCCl_3$.

31. The process as claimed in claim 29, wherein the reaction is carried out under acid or base catalysis.

32. A process for producing a compound of formula I, which comprises:
reacting a hydroxynitrile of the formula IV

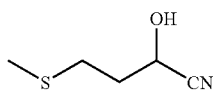

(IV)

with a carbonyl compound $R^1R^2C=O$ in the presence of an acid and a carboxylic anhydride, to obtain the compound of the formula I as claimed in claim 8;
wherein X=NH; and
$R^1$ and $R^2$ have the meaning given in claim 8.

33. The process as claimed in claim 32, wherein the acid is sulfuric acid, acetic acid or mixtures thereof; and wherein the carboxylic anhydride is acetic anhydride.

34. A process for producing a compound of formula I, which comprises:
reacting a compound of the general formula III

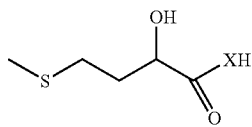

(III)

with a carbonyl compound $R^1R^2C=O$ in free or acetalated form, optionally in the presence of a solvent, to obtain a compound of formula I as claimed in claim 8;
wherein X, $R^1$ and $R^2$ each have the meaning given in claim 8.

35. A process for producing a compound of formula II, which comprises:
reacting a compound of the general formula III

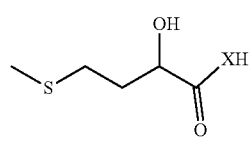

(III)

with a carbonic acid derivative $X^1X^2C=O$, to obtain a compound of formula II as claimed in claim 16;
wherein $X^1$ and $X^2$ are identical or different and independent of one another can be chlorine or $OCCl_3$; $OCH_3$, $OCH_2CH_3$, or imidazolyl or triazolyl bound via a nitrogen in the molecule.

36. The compound as claimed in claim 1, having the formula I, wherein X=NH.

* * * * *